US012668527B2

(12) United States Patent
Xia et al.

(10) Patent No.: US 12,668,527 B2
(45) Date of Patent: Jun. 30, 2026

(54) GLASS CERAMICS AND METHODS OF MAKING SUCH

(71) Applicant: INSTITUT STRAUMANN AG, Basel (CH)

(72) Inventors: Wei Xia, Uppsala (SE); Le Fu, Hunan (CN); Håkan Engqvist, Uppsala (SE)

(73) Assignee: INSTITUT STRAUMANN AG, Basel (CH)

( * ) Notice: Subject to any disclaimer, the term of this patent is extended or adjusted under 35 U.S.C. 154(b) by 914 days.

(21) Appl. No.: 17/800,009

(22) PCT Filed: Feb. 17, 2021

(86) PCT No.: PCT/EP2021/053839
§ 371 (c)(1),
(2) Date: Aug. 16, 2022

(87) PCT Pub. No.: WO2021/165293
PCT Pub. Date: Aug. 26, 2021

(65) Prior Publication Data
US 2023/0072504 A1     Mar. 9, 2023

(30) Foreign Application Priority Data

Feb. 17, 2020    (SE) .................................... 2050178-9

(51) Int. Cl.
| | |
|---|---|
| *C03C 10/00* | (2006.01) |
| *A61K 6/833* | (2020.01) |
| *C03C 3/083* | (2006.01) |
| *C03C 4/00* | (2006.01) |
| *C03C 14/00* | (2006.01) |

(52) U.S. Cl.
CPC .......... *C03C 10/0009* (2013.01); *A61K 6/833* (2020.01); *C03C 3/083* (2013.01); *C03C 4/0021* (2013.01); *C03C 14/006* (2013.01); *C03C 2205/06* (2013.01); *C03C 2214/32* (2013.01)

(58) Field of Classification Search
CPC ...................................................... A61K 6/833
See application file for complete search history.

(56) References Cited

U.S. PATENT DOCUMENTS

| | | | |
|---|---|---|---|
| 2009/0061195 A1* | 3/2009 | Kasai | .................... C03C 14/002 428/220 |
| 2010/0130346 A1 | 5/2010 | Laine et al. | |
| 2014/0205972 A1 | 7/2014 | Xia | |

FOREIGN PATENT DOCUMENTS

| | | |
|---|---|---|
| WO | WO2014/101997 A1 | 7/2014 |
| WO | WO 2018/093322 | 5/2018 |

OTHER PUBLICATIONS

Vagkopoulou et al., "Zirconia in dentistry: Part 1. Discovering the nature of an upcoming bioceramic.", Clinical Research, The European Journal of Esthetic Dentistry, vol. 4, No. 2, 2009, pp. 3-22.
(Continued)

*Primary Examiner* — Benjamin L Utech
(74) *Attorney, Agent, or Firm* — Dority & Manning, P.A.

(57)     ABSTRACT

The present invention relates to a glass ceramic material comprising a core-rim structure, wherein the core-rim structure comprises an amorphous $SiO_2$ matrix, $ZrO_2$ crystals, and hardness-enhancing additive, the $ZrO_2$ crystals are present in cores that are at least partly surrounded by a rim comprising hardness-enhancing additive.

16 Claims, 11 Drawing Sheets

(56)         References Cited

OTHER PUBLICATIONS

PCT International Search Report and Written Opinion for corresponding PCT Application No. PCT/EP2021/053839, mailed on May 31, 2021, 11 pages.
Fu et al. "Highly translucent and strong ZrO2-SiO2 nanocrystalline glass ceramic prepared by sol-gel method and spark plasma sintering with fine 3D microstructure for dental restoration," *Journal of the European Ceramic Society*, vol. 37, No. 13, May 25, 2017, pp. 4067-4081 (Abstract only).
Japanese Office Action (w/ English translation) for corresponding Application No. 2022-549195, dated Aug. 8, 2023, 8 pages.

* cited by examiner a)

b)

a)

b)

a)

b)

c)

a)

2 theta (degrees)

b)

2 theta (degrees)

c)

2 theta (degrees)

a)

b)

c)

d)

e)

a)

b)

c)

GLASS CERAMICS AND METHODS OF MAKING SUCH

CROSS-REFERENCE TO RELATED APPLICATIONS

This application is a national stage application of PCT international application PCT/EP2021/053839, filed on Feb. 17, 2021, which claims priority to Swedish Patent Application No. 2050178-9, filed on Feb. 17, 2020, both of which are hereby incorporated by reference in their entireties for all purposes.

FIELD OF THE INVENTION

The present invention relates to a glass ceramic material, more particularly to a glass ceramic material and methods of producing such a material, as well as densified material for e.g. dental restorative purposes.

BACKGROUND OF THE INVENTION

Due to their mechanical properties and appealing aesthetics, ceramics and glass ceramics are widely used as dental materials. Today, ceramic materials are used in all types of indirect dental restorations: no-preparation veneers, thin veneers, bridges, multi-unit posterior fixed partial dentures (FPDs), etc.

One of the main advantages with glass ceramics is their translucency, which enables a high flexibility of the colour and the material can more easily be adapted the colour of the surrounding teeth.

Zirconia ($ZrO_2$)-based ceramics are among the most well-studied dental materials due to their good mechanical properties, they are known as "ceramic steel", as well as being biocompatible. However, the high strength often comes with less good aesthetic properties, resulting in a more opaque material.

"Glass preparation of the $ZrO_2$—$SiO_2$ system by the sol-gel process from metal alkoxides" by M. Nogami in J. Non-Cryst. Sol. 69 (1985) 415-423 discloses glasses in the $ZrO_2$—$SiO_2$ system containing up to 50 mol % $ZrO_2$. The density, refractive index and hardness were all observed to increase with increasing $ZrO_2$ content.

EP 3541760 discloses a process for producing translucent $ZrO_2$—$SiO_2$ nanocrystalline glass ceramic with ultra-high flexural strength by pressure-assisted sintering or pressureless sintering.

In view of the prior art, there is a need for an enhanced glass ceramic composition with improved hardness, as well as pleasing aesthetic properties such as translucency and ability to resemble natural teeth, and a method for making such a composition, and a dental restorative material comprising such a composition.

SUMMARY OF THE INVENTION

The object of the present invention is to provide an improved glass ceramic material having a high strength and good translucency and a method of making such a material, this is achieved by the material in claim 1 and the method in claim 11.

According to one aspect of the invention there is a glass ceramic material comprising zirconium dioxide crystals embedded in an amorphous silicon dioxide matrix and at least one hardness enhancing additive. The zirconium dioxide crystals form cores and the cores are at least partly surrounded by rims, wherein the rims comprise an intergranular phase, and wherein the intergranular phase comprises at least silicon dioxide, zirconium dioxide and at least one hardness-enhancing additive. The concentration in weight percent of the hardness-enhancing additive is higher in the rims than in the amorphous silica matrix and in the cores.

According to one embodiment at least a portion of the cores are connected with at least one adjacent other core forming a grain boundary between the cores. The concentration of hardness-enhancing additive oxide is higher in the grain boundaries than in the parts of the rim in connection with the silicon dioxide matrix.

According to a second aspect of the invention there is a method of forming a glass ceramic material wherein the method comprises the following steps:

11: mixing of two sols, the first sol comprises a zirconium dioxide precursor material and the second sol comprises a silicon dioxide precursor material, adding a catalyst to the mixture of two sols, and wherein said step comprises adding a precursor material for a hardness-enhancing additive;

12: drying and forming of a xerogel;

13: calcination of the formed xerogel; and

14: sintering of the calcined xerogel;

wherein the method comprises a fractionation step reducing the particle size of the material.

According to a third aspect of the invention there is a densified material comprising a glass ceramic material.

According to a fourth aspect of the invention there is a dental restorative material comprising a densified material comprising a glass ceramic material.

In the following, the invention will be described in more detail, with examples and depending claims.

DEFINITIONS AND ABBREVIATIONS

Figure 1:
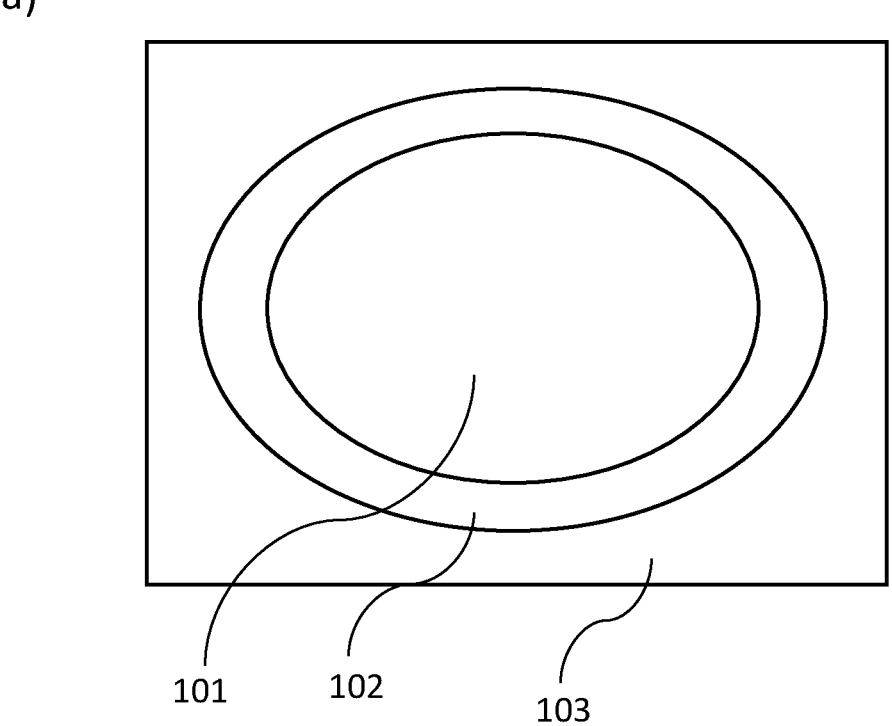
FIGS. 1 *a* and *b* are schematic illustrations of structures according to the invention.
Figure 1:
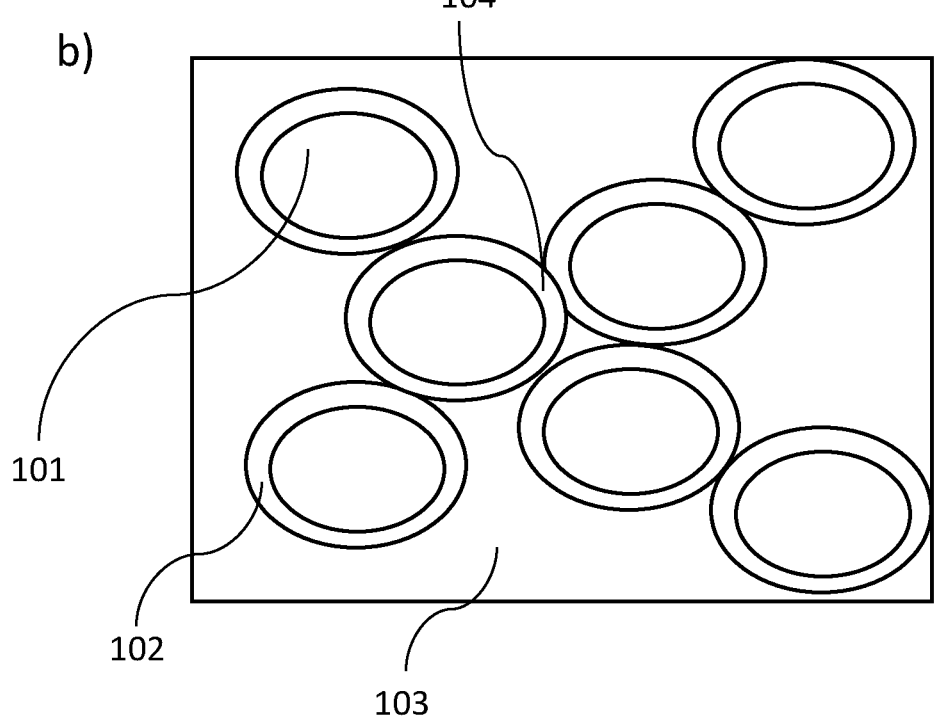

The terms 'nGC' or 'nGCs' is short for nanocrystalline glass ceramic(s), herein comprising $ZrO_2$ and $SiO_2$;

the term 'c-$ZrO_2$' is short for cubic $ZrO_2$;

the term 'm-$ZrO_2$' is short for monoclinic $ZrO_2$;

the term 't-$ZrO_2$' is short for tetragonal $ZrO_2$;

the term 'PXRD' is short for powder X-ray diffraction;

the term 'SPS' is short for spark-plasma sintering;

the term 'HIP' is short for hot isostatic pressing;

the term 'mol %', or molar %, or molar fraction, is the amount of a constituent expressed in moles divided by the total amount of all constituents in a composition expressed in moles;

the term 'at %' is the amount of a constituent expressed in atoms divided by the total amount of all constituents in a composition expressed in atoms;

the term 'wt %', or weight %, or weight fraction is the weight of a constituent divided by the total weight of all constituents in a composition;

the term 'GB' is short for grain boundary;

the term 'IGF' is short for intergranular phase;

the term 'HP' is short for hot pressing; and the term 'STEM' is short for scanning transmission electron microscopy.

DETAILED DESCRIPTION

Glass ceramics of zirconia-silica ($ZrO_2$—$SiO_2$) comprises nano-sized $ZrO_2$ crystals embedded in an amorphous matrix of $SiO_2$, such materials may be described as nanocrystalline glass ceramics (nGCs). Such materials are interesting for dental applications. However, there is a need for improvement of the hardness of such materials. Additionally, a dental material should preferably be optically translucent, since it will then appear more similar to natural teeth as compared to an opaque material, as well as being easier to color. Ideally, a dental material should be both hard and optically translucent.

Hardness is a mechanical property of the material, which can be tested in terms of microhardness and nanohardness. Microhardness is obtained by "microindentation hardness testing" and testing the hardness of the material on a microscopic scale. Nanohardness is obtained by "nanoindentation hardness testing", testing the hardness on a micro- or even nanometer scale using a very small tip size for the indentation object used. Other mechanical properties include Young's modulus and fracture toughness. Young's modulus measures the stiffness of a material, and defines the relationship between stress and strain. Fracture toughness is a measure of the stress required in a material for a crack to propagate rapidly. It is of interest to improve, i.e. increase the hardness (micro and nano) and possible also other important mechanical or optical properties of the materials. Biaxial strength is the stress at failure in bending, and represents the highest stress experienced within the material at its moment of yield.

In order to improve the hardness, while still keeping the translucency of a glass ceramic material comprising $ZrO_2$ crystals and amorphous $SiO_2$ at an acceptable level at least one hardness enhancing additive is added to the material. A majority of the $ZrO_2$ crystals are connected with adjacent crystals forming grain boundaries (GBs) in at least one direction.

Figure 5:
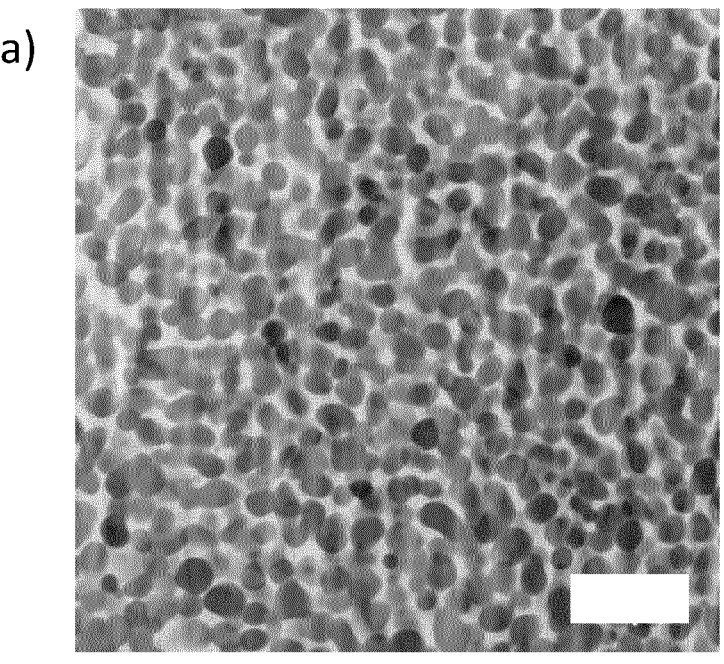
FIGS. 5 *a* and *b* are STEM images of one embodiment of the invention, a) including a 200 nm scale bar and b) including a 50 nm scale bar.
Figure 5:
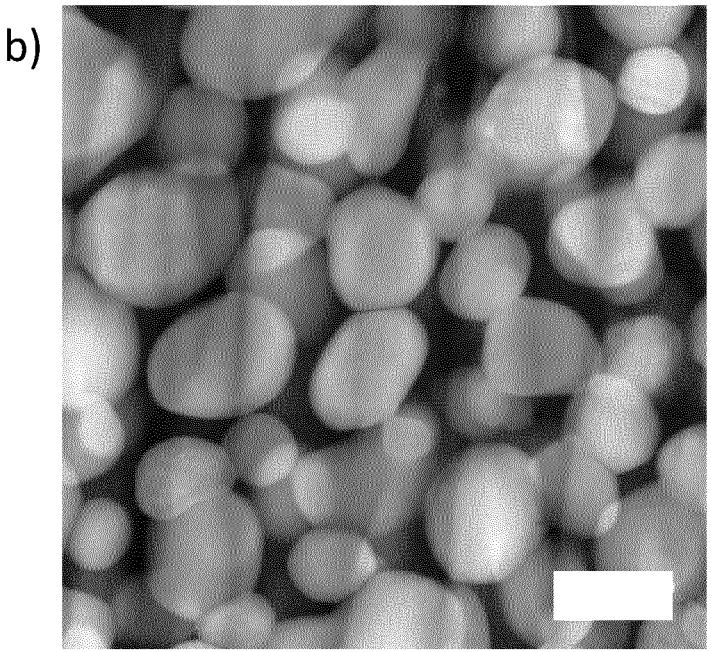

The above described microstructure is schematically illustrated in FIGS. 1 *a* and *b*, wherein cores 101 are surrounded by rim 102, the cores 101 with the rims 102 arranged in an amorphous $SiO_2$ matrix 103. The $ZrO_2$ crystals form the cores 101. The rims 102 comprises an intergranular phase (IGF) that comprises $SiO_2$, $ZrO_2$, and at least one hardness enhancing additive oxide. Most of the cores 101 are arranged close to another core 101 forming a grain boundary (GB) 104 in at least one direction. The GBs comprise IGF. The microstructure is further shown in for example the scanning transmission electron microscopy (STEM) micrographs in FIGS. 5*a* and *b*. In FIG. 5*a* the parts with darker contrast are the $ZrO_2$ crystals (the cores 101), while the 'background' with brighter contrast corresponded to the amorphous $SiO_2$ matrix 103. In FIG. 5*b*, the parts with bright contrast are $ZrO_2$ crystals (the cores 101) while the darker background is amorphous $SiO_2$ matrix 103.

As a general description a nanocrystalline glass ceramic material with core-rim structure is provided that comprises an amorphous $SiO_2$ matrix 103, $ZrO_2$ crystals and hardness-enhancing additive wherein the $ZrO_2$ crystals are present in cores 101 that are at least partly surrounded by a rim 102, wherein the rim 102 comprises the hardness-enhancing additive.

As described above, the at least one hardness enhancing additive is present in the rims 102, i.e. in the IGF in the GBs between at least two adjacent crystals (i.e. cores 101) and on the surface of the crystals (i.e. cores 101). In other words the at least one hardness enhancing additive, for example in the form of an oxide, exists at the $ZrO_2$/$ZrO_2$ interface and at the $ZrO_2$/$SiO_2$ interface. The concentration in weight % of at least one hardness enhancing additive is higher in the GB than in the $ZrO_2$/$SiO_2$ interface.

Figure 6:
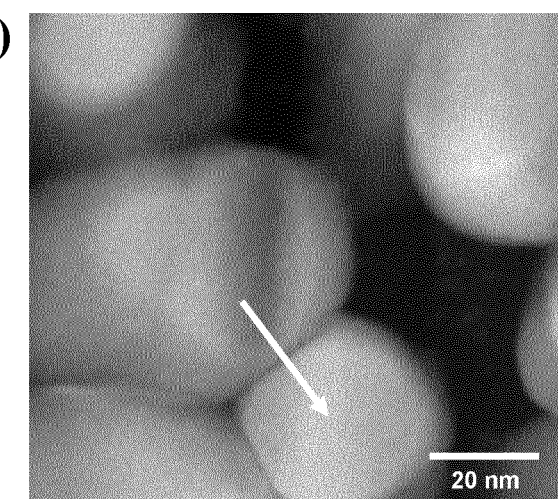
FIGS. 6 *a-c* are graphs showing line scans of one embodiment of the invention, a) is a STEM image with a 20 nm scale bar, b) is a graph showing the atomic ratio and c) is a graph showing the atomic ratio.
Figure 6:
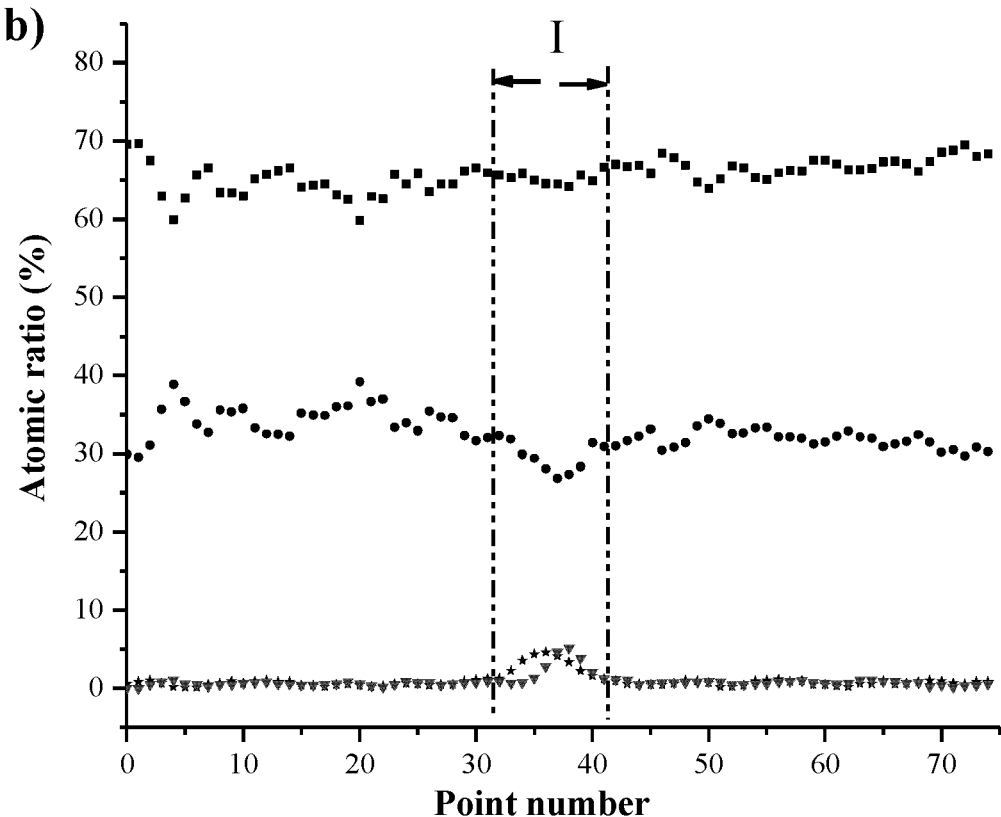
Figure 6:
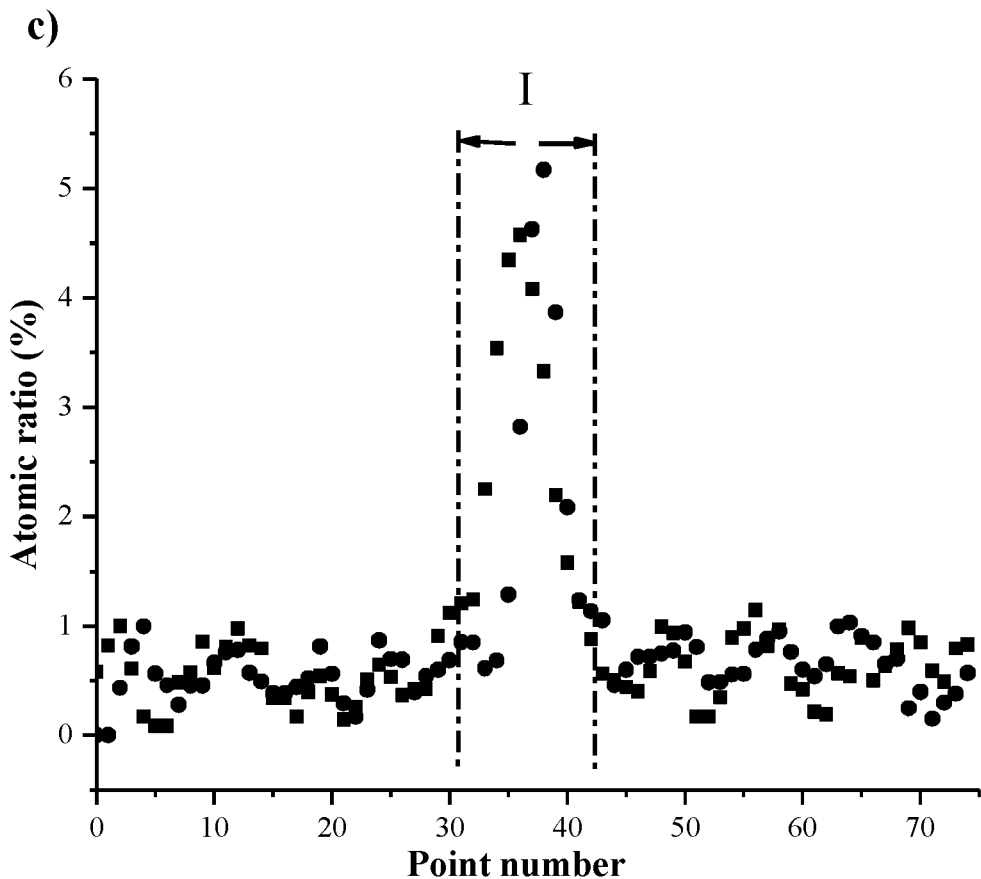

At least in terms of hardness it is an advantage that the hardness-enhancing additive oxide in the GBs is amorphous, and/or that the IGF is amorphous. FIG. 6*a* shows STEM micrographs of connecting $ZrO_2$ crystals (brighter parts) arranged in a $SiO_2$ matrix (darker part). In between the connecting $ZrO_2$ crystals is an IGF.

In a glass ceramic material according to the invention at least a majority of the $ZrO_2$ crystals are single crystalline, meaning that the crystals themselves does not comprise any GBs. This may be advantageous in terms of optical properties.

A glass ceramic material according to the invention comprises a majority of $ZrO_2$, as compared to the other components, in terms of both molar % and wt %. In one embodiment a nGC material comprise 50-80 molar % of $ZrO_2$ or 35-85 weight % of $ZrO_2$. The $ZrO_2$ crystals, i.e. the cores 101, form a network in the amorphous $SiO_2$ matrix 103, wherein the majority of the $ZrO_2$ crystals are connected to at least one other $ZrO_2$ crystal forming GBs 104 in at least one direction. Without being bound to any theory, the network of $ZrO_2$ crystals connected by GBs comprising IGF may act as a structural reinforcer to the material so that hardness of the material increases.

A glass ceramic material according to the invention is schematically illustrated in FIGS. 1*a* and *b*. In one embodiment a glass ceramic material illustrated in FIGS. 1*a* and *b* comprises an amorphous $SiO_2$ matrix 103, $ZrO_2$ crystals and hardness-enhancing additive. The cores 101 are comprised of one or more $ZrO_2$ crystals that are at least partly surrounded by a rim 102, which comprises hardness-enhancing additive.

The hardness-enhancing additive is a chemical element or composition or a mixture of different compositions or elements, e.g. $Al_2O_3$ or $Y_2O_3$. In particular it may be an oxide or a mixture of oxides. The hardness-enhancing additive may be present as nano-sized domains adjacent to the $ZrO_2$ crystals, i.e the cores 101, i.e. not as a continuous ring but rather as connecting areas of hardness-enhancing additive oxide, or IGF, surrounding the $ZrO_2$ crystal, or core 101.

This can further be seen in the STEM micrograph in FIG. 8*d* for example wherein nanodomains of $Al_2O_3$ are arranged adjacent to the $ZrO_2$ crystal.

Without being bound by any theory, the IGF arranged at the rim 102, i.e. at the surface of the $ZrO_2$ crystals and in the GBs, may act as an interface enhancement such that the $ZrO_2$ stays inside the crystals and does not migrate to the amorphous matrix 103.

$ZrO_2$ can exist in three different phases: monoclinic (m), tetragonal (t) and cubic (c). The $m-ZrO_2$ phase is the most stable of these. It is formed at room temperature and transitions to the $c-ZrO_2$ phase at higher temperatures. The transition occur via the $t-ZrO_2$ phase. While $m-ZrO_2$ is the most stable phase, $t-ZrO_2$ is mechanically the strongest phase and hence suitable to have in a dental material. A nGC material according to the invention may comprise $ZrO_2$ in the form of $t-ZrO_2$ and $m-ZrO_2$, the majority being $t-ZrO_2$. In one embodiment a nGC material may comprise 80-95 wt % $t-ZrO_2$ and 5-20 wt % of $m-ZrO_2$. In one embodiment the zirconium dioxide comprises either tetragonal zirconium dioxide or a mixture of tetragonal zirconium dioxide and monoclinic zirconium dioxide, wherein at least 80% of the zirconium dioxide crystals are tetragonal zirconium dioxide, as determined by Rietveld refinement.

Without being bound by any theory, the $t-ZrO_2$ crystals may be stabilized in their tetragonal phase by the amorphous $SiO_2$ matrix. It is advantageous in dental applications that a glass ceramic material comprises a majority of $t-ZrO_2$ as compared to the other $ZrO_2$ phases. In further embodiments, the $ZrO_2$ comprises $t-ZrO_2$, for example 80-100 wt % and 0-20 wt % of $m-ZrO_2$. The amount of the different crystalline phases can for example be determined by Rietveld refinement of powder X-ray diffractogram data.

In one embodiment of the first aspect of the invention, the glass ceramic material comprises 1.5-10 molar % of hardness-enhancing additive oxide. In other embodiments, the glass ceramic material comprises 2.5-10 molar % additive, or 2.5-7.5 molar % additive, or 2.5-5 molar % additive, or 5-5.5 molar % additive, or 5-7.5 molar % additive, or 1.5-9 molar % additive, or 1.5-7.5 molar % additive, or 1.5-12 molar % additive, or 1.5-5 molar % additive, or 3.5-10 molar % additive, or 3.5-7.5 molar % additive, or 3.5-6 molar % additive, or 3.5-5 molar % additive, or 1.5-4.5 molar % additive, or 2-4.5 molar % additive, or 2.5-4 molar % additive, or 4.5-10 molar % additive.

In one embodiment of the first aspect of the invention, the glass ceramic material comprises 2-10 weight % of hardness-enhancing additive, preferably in the form of an oxide. In other embodiments, the glass ceramic material comprises 2.5-10 weight % additive, or 2.5-7.5 weight % additive, or 2.5-6 weight % additive, or 4-7.5 weight % additive, or 2.5-5 weight % additive, preferably in the form of yttrium oxide or aluminum oxide, or a combination thereof.

The hardness-enhancing additive(s) in the final material relates to the molar % or weight % of hardness-enhancing additive in oxide form. In some embodiments it relates to $Y_2O_3$ or $Al_2O_3$ in the material, or a combination thereof. In one embodiment the hardness-enhancing additive comprises aluminum oxide or yttrium oxide, or a combination of aluminum oxide and yttrium oxide.

In one embodiment of the first aspect of the invention the glass ceramic material comprises $ZrO_2$ crystals, i.e. cores 101, wherein at least 90%, or at least 95% of the crystals have an average crystal size of 100 nm or less. The $ZrO_2$ crystals may be approximately 20-100 nm or 40-60 nm in diameter at the longest diameter. The diameter of the $ZrO_2$ crystals, i.e. the size of the crystals, may impact both the optical properties and the mechanical properties. For example, crystals larger than 1 µm may result in a more opaque nGC material. For at least that reason it may be advantageous that the $ZrO_2$ crystals are not too large, i.e. that the diameters of the $ZrO_2$ crystals are 100 nm or less. The crystal size, i.e. the diameter, can be determined using for example pXRD or TEM or any other suitable technique.

In one embodiment the cores 101 are at least partly surrounded by rims 102, such that at least 50 vol % of the circumference of a core 101 is in contact with a rim 102. The rim 102 is approximately 5-20 nm thick and comprises at least one type of hardness-enhancing additive, oxygen, zirconium, and silicon. The concentration in wt % of hardness-enhancing additive is higher in the rim 102 than in the other parts of the composition. The hardness-enhancing additive is a compound or compounds, preferably in oxide form, other than $SiO_2$ and $ZrO_2$. It can also be a combination of compounds.

The $ZrO_2$ crystals, i.e. the cores 101, may comprise up to 5 mol %, of the hardness-enhancing additive due the solid solution between Zr and the hardness-enhancing additive.

In one embodiment of the first aspect, the $ZrO_2$ crystals, i.e. the cores 101, have an ellipsoidal shape. In one embodiment of the first aspect, the majority of the $ZrO_2$ crystals, i.e. the cores 101, have an ellipsoidal form, i.e. an ellipsoidal morphology. In another embodiment of the first aspect, the $ZrO_2$ crystals comprises $t-ZrO_2$.

An ellipsoidal morphology may enable an improved package density as compared with e.g. a spherical morphology. It may also enable an improved 3D network of $ZrO_2$ in the $SiO_2$ matrix 103, which may increase the hardness of the nCG material.

In one embodiment of the first aspect, the hardness-enhancing additive comprises aluminum oxide or yttrium oxide, or a combination of aluminum oxide and yttrium oxide.

In one embodiment of the first aspect, the intragranular phase is amorphous.

In one embodiment of the first aspect, the IGF comprises yttrium (Y) cations, or aluminium (Al) cations, or their respective oxides ($Y_2O_3$ and $Al_2O_3$), or a combination of either of these. It is advantageous at least in terms of hardness of the glass ceramic material that the IGF is amorphous. Both $Y_2O_3$ and $Al_2O_3$ are advantageous to use as a hardness-enhancing additive since they may increase the hardness and the Young's modulus of a nGC material.

In one embodiment of the first aspect, the IGF comprises manganese (Mn) cations, or magnesium (Mg) cations, or cerium (Ce) cations or any of their respective oxides (MnO, $Mn_3O_4$, $Mn_2O_3$, $MnO_2$, $MnO_3$, $Mn_2O_7$, MgO, $Ce_2O_3$, $Ce_3O_4$ and $CeO_2$), or a combination of either of these. It is advantageous at least in terms of hardness of the glass ceramic material that the IGF is amorphous. The amounts and preferred amounts of these hardness-enhancing additives (Mn, Mg, and Ce) are the same as given for $Y_2O_3$ or $Al_2O_3$, when taking into consideration the number of cations per mol for each of the additives of the finished product. For example, if the amount of $Y_2O_3$ in the finished product would be 5 molar %, or 10-12 wt % then the corresponding amount of MnO would be 10 molar %, or 10-12 wt % and for $CeO_2$ it would be 3.3 molar %, or 5-7 wt %.

In one example of the first aspect, the IGF comprises yttrium (Y) cations, or aluminium (Al) cations, or its respective oxides ($Y_2O_3$ and $Al_2O_3$), or a combination of either of these, in combination with one or more of manganese (Mn) cations, magnesium (Mg) cations, cerium (Ce) cations or any of their respective oxides (MnO, $Mn_3O_4$, $Mn_2O_3$, $MnO_2$, $MnO_3$, $Mn_2O_7$, MgO, $Ce_2O_3$, $Ce_3O_4$ and $CeO_2$).

In one embodiment of the first aspect, the IGF comprises yttrium oxide.

In one embodiment of the first aspect, the nGC comprises amorphous $Y_2O_3$ as hardness-enhancing additive, forming a $Y_2O_3$—$ZrO_2$—$SiO_2$ material.

In a $Y_2O_3$—$ZrO_2$—$SiO_2$ material, the $ZrO_2$ may be in the form of crystalline particles, 101, embedded in an amorphous $SiO_2$ matrix 103. The yttrium component (e.g. cation or oxide) in the $Y_2O_3$—$ZrO_2$—$SiO_2$ material is present in the rim 102. It may also be present inside the $ZrO_2$ crystal lattice, as discussed above.

In one embodiment of the first aspect, the nGC material comprises 1.5-5 mol % $Y_2O_3$, 20-42 mol % $SiO_2$ and 55-77 mol % $ZrO_2$, or 4-8 wt % $Y_2O_3$, 35-85 wt % $SiO_2$, and 10-60 wt % $ZrO_2$ In one embodiment of the first aspect, the hardness-enhancing additive comprises aluminum oxide.

In one embodiment of the first aspect the nGC comprises $Al_2O_3$ as hardness-enhancing additive, forming a $Al_2O_3$—$ZrO_2$—$SiO_2$ material.

In an $Al_2O_3$—$ZrO_2$—$SiO_2$ material the $ZrO_2$ may be in the form of crystals, i.e. cores 101, embedded in an amorphous $SiO_2$ matrix 103. The $Al_2O_3$ in the $Al_2O_3$—$ZrO_2$—$SiO_2$ material is present in the rim 102. It may additionally be present to some extent in the $SiO_2$ matrix 103.

In one embodiment of the first aspect the nGC material comprises 1.5-7.5 mol % $Al_2O_3$ or 2.5-5 mol % $Al_2O_3$, 20-40 mol % $SiO_2$ and 55-75 mol % $ZrO_2$, or 2.5-5 wt % $Al_2O_3$, 15-35 wt % $SiO_2$, and 60-80 wt % $ZrO_2$.

One advantage of nCG materials comprising $Al_2O_3$ as a hardness-enhancing additive in the IGF is that the $Al_2O_3$ may increase the fracture toughness of the nCG material. Fracture toughness is a way of expressing the material's resistance to crack propagation.

All variants and examples of the first aspect can be combined with the second and third aspects unless expressly stated otherwise.

In a second aspect of the invention there is a method of forming a glass ceramic wherein the method comprises the following steps:

11: mixing of two sols; one comprising a $ZrO_2$ precursor material and one comprising a $SiO_2$ precursor material, adding a catalyst to the mixture of two sols, and forming a gel, and wherein said step comprises adding a precursor material for a hardness-enhancing additive;
  12: drying and forming a xerogel;
  13: calcination of the xerogel; and
  14: sintering of the calcined xerogel;
  wherein the method comprises a fractionation step reducing the particle size of the material.

The fractionation step of the method relates to reducing the particle size of the material. This may achieved by using the drying method in step 12 that reduces the particle size or by milling the xerogels formed after step 12 or 13. In such a case the xerogel will be formed into a powder.

A nGC material according to the invention may be prepared in a sol-gel process. In such a sol-gel process, a powder is formed, which may subsequently be sintered to form a final structure.

Sol-gel processes or methods are well-known techniques in inorganic chemistry to form solid materials from small molecules. The process generally involves the conversion of monomers into a colloidal solution, i.e. a sol, that acts as the precursor for an integrated network, i.e. a gel. The gel may be composed of small particles or a network of polymers.

After a sol-gel process, an inorganic, solid, powder is formed. The formed powder may be sintered to form a solid body. Sintering is a process, or method, of compacting and forming a solid from a powder by heat and/or pressure without including melting. The powder formed in the sol-gel process may be compacted with or without heating prior to being sintered. It may also be compacted during sintering.

Figure 2:
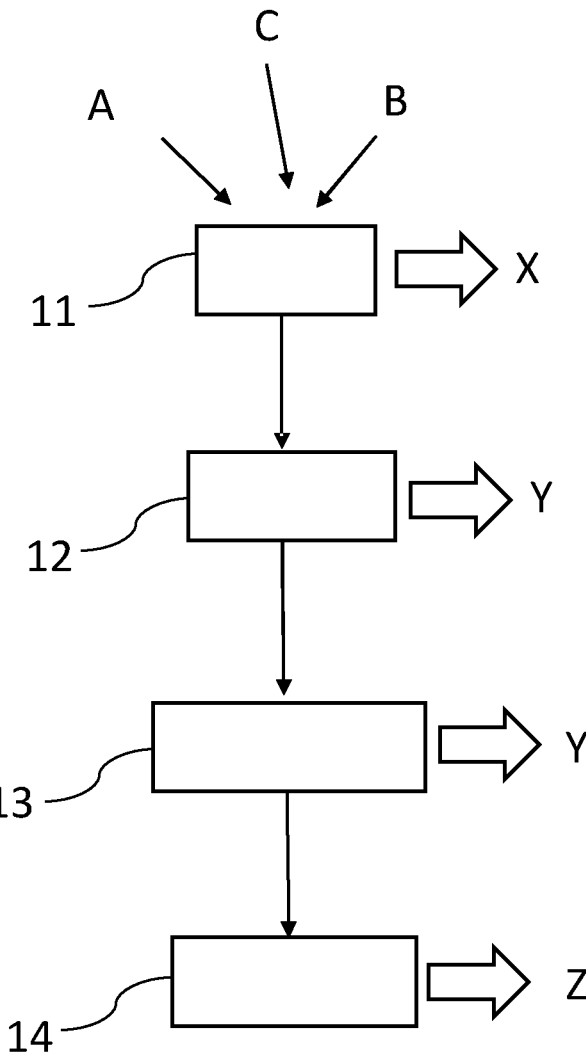
FIG. 2 is a flow-chart according to one embodiment of the invention.

A nGC material according to the invention can be synthesized using a sol-gel method comprising the following sequential steps, see FIG. 2:

11: two sols are mixed (marked A and B in FIG. 2), one comprising a $ZrO_2$ precursor material and one comprising a $SiO_2$ precursor material, a catalyst is added to the mixture of the two sols. The precursor hardness-enhancing additive material (marked C in FIG. 2) can be added to either of the two sols or to the mixture after the two sols have been mixed, but preferably it is added to the sol comprising the $ZrO_2$ precursor in order to at least partly avoid precipitation of the $ZrO_2$ precursor. After the two sols have been mixed, they form a gel (marked X in FIG. 2);
  12: the formed gel is dried, forming a xerogel (marked Y in FIG. 2), but may, depending on the drying method, form a powder;
  12': the formed xerogel may be milled into a powder with a defined particle size distribution, e.g. 1-25 μm, or 25-500 μm, or 25-250 μm, or 50-100 μm, or milled after a calcination step as step 13';
  13: the formed xerogel or powder is calcined in order to remove organic residues; and
  13': if still being a xerogel (marked Y in FIG. 2) after step 13, then the zerogel is milled into a powder;
  14: the calcined powder is sintered, forming a solid product (marked Z in FIG. 2).

In one embodiment, step 12' or 13' is part of the process. In other embodiment, if e.g. a different drying process is used in step 12, then step 12' or 13' may become optional if said reduction of particle size (fractionation) is achieved in the drying process. Examples of different drying processes are evaporation of the sol or spray drying.

Examples of $SiO_2$ precursor materials in step 11 are tetraethyl orthosilicate (TEOS), ethyl silicate, and silicon alkoxides. Examples of $ZrO_2$ precursor materials in step 11 are zirconium propoxide or $Zr(OPr)_4$, zirconyl nitrate, $ZrOCl_2$ solution, and zirconium (IV) chloride.

The catalyst may be acidic. Examples of suitable catalysts are hydrochloride acid, nitric acid, citric acid, acetic acid, ethylenediaminetetraacetic acid, tartaric acid, glycolic acid, oxalic acid, malic acid, and formic acid.

Examples of precursor materials for additives are $Al(O$-$i$-$Pr)_3$ for aluminium and $YCl_3$ for yttrium. Other examples include aluminium-sec butoxide or $Al(OBu)_3$, $AlCl_3$, $Al(NO_3)_3.9H_2O$ and $Y(NO_3)_3$, yttrium acetate, yttrium oxo-isopropoxide or $Y_5O(OPri)_{13}$, $Y_2(SO_4)_3$, yttrium isopropoxide or $C_9H_{21}O_{13}Y$.

The precursor material for the hardness-enhancing additive may constitute 3-20 molar % of the total amount of the precursor materials $ZrO_2$, $SiO_2$, and hardness-enhancing additive, calculated as the content of $Y^{3+}$ or $Al^{3+}$ or a combination thereof. In one embodiment of the second aspect of the invention, the glass ceramic material comprises 2-20 molar % hardness-enhancing additive. In other embodiment, the glass ceramic material comprises 5-20 molar % hardness-enhancing additive, or 5-15 molar % hardness-enhancing additive, or 5-10 molar % hardness-enhancing additive, or 10-20 molar % hardness-enhancing additive, or 10-15 molar % hardness-enhancing additive, or 3-18 molar % hardness-enhancing additive, or 3-15 molar % hardness-enhancing additive, or 3-12 molar % hardness-enhancing additive, or 3-10 molar % hardness-enhancing additive, or 7-20 molar % hardness-enhancing additive, or 7-15 molar % hardness-enhancing additive, or 7-12 molar % hardness-enhancing additive, or 7-10 molar % hardness-enhancing additive, or 3-9 molar % hardness-enhancing additive, or 4-9 molar % hardness-enhancing additive, or 5-8 molar % hardness-enhancing additive, or 9-20 molar % hardness-enhancing additive.

The amounts and preferred amounts of the other precursors for the hardness-enhancing additives (Mn, Mg, and Ce) are the same as given for $Y_2O_3$ or $Al_2O_3$, when taking into consideration the number of cations per mol for each of the precursor materials for the hardness-enhancing additives. For example, if the amount of $Y^{3+}$ in the precursor material for the hardness-enhancing additive would be 5 molar %, then the corresponding amount of $Mn^{3+}$ would be 5 molar %.

Different solvents can be used in the sol-gel method 10, for example ethanol, methanol, anhydrous 1-propanol and isopropanol. It is important to control the pH in the different steps of the sol-gel method, in order to at least partly control the gelation process and to dissolve the precipitates. This can for example be done by dripwise addition of HCl to the sol(s) and also during the different steps of the reaction. The rate of the dripping may be varied.

Figure 3:
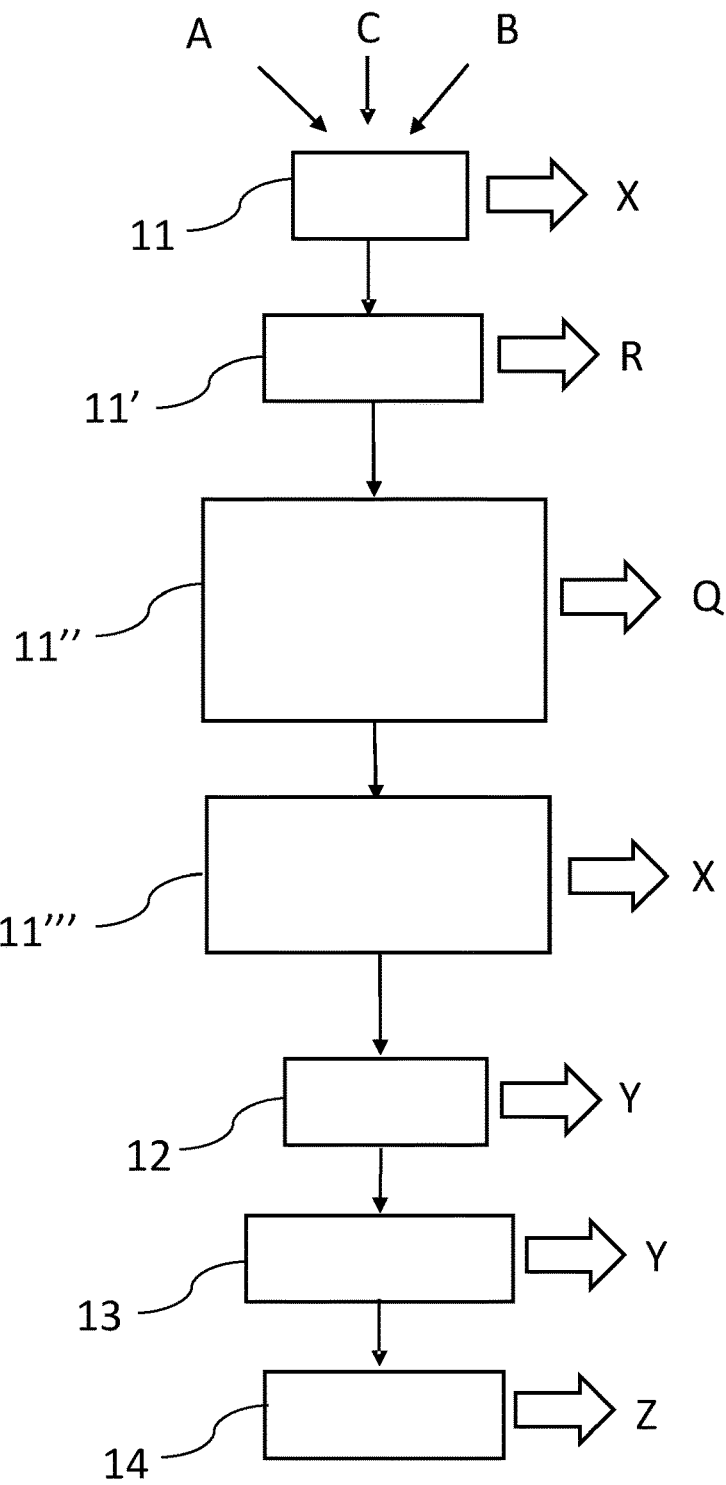
FIG. 3 is a flow-chart according to one embodiment of the invention.

In one embodiment of the second aspect, step 11 may comprise additional steps 11', 11", and 11''', see FIG. 3. FIG. 3 uses the same marks as FIG. 2, i.e. the two sols are marked A and B, the additive is marked C, gel is marked X, xerogel is marked Y, and solid product is marked Z.

Step 11' comprises heating, wherein a pseudogel (marked R in FIG. 3) is formed after the two sols have been mixed and heated. It may automatically form a clear sol after some time, but in in optional step 11", the pseudogel is kept at an elevated temperature, e.g. 50-70° C., for a time period of 10-15 h after which it forms a clear sol (marked Q in FIG. 3). In optional step 11''', an acid is added to the clear sol in step 11''', after which a gel is formed that is dried in step 12 to a xerogel.

In one embodiment of the second aspect, the sintering in step 14 of the method is performed using hot isostatic pressure (HIP), or spark plasma sintering (SPS).

SPS has a high heating rate as compared to other sintering techniques, which can be used to limit or avoid grain growth at relatively low sintering temperatures.

HIP and HP are other manufacturing techniques that can be used to increase the density of a ceramic material. This is achieved by applying both heat and pressure.

Before the sintering step, the powder may be compacted to increase the density of the material after sintering. Optionally, the packing density can be further enhanced by addition of a step of granulation before the compaction and/or sintering. Examples of methods of powder granulation are spray drying, extrusion and spherinizer, reverse wet granulation, steam granulation, moisture-activated dry granulation, thermal adhesion granulation, freeze granulation, foam granulation. The granulation method should form granules having a granule size of 50 μm to 1 mm.

All variants and examples of the second aspect can be combined with the first and third aspect unless expressly stated otherwise.

In a third aspect of the invention, there is a densified material comprising a glass ceramic material.

In general, in the dental art, a densified material has the meaning of a material that has a density of 90% or more of the theoretical density.

In the third aspect of the invention there is a densified glass ceramic material comprising $ZrO_2$ crystals, forming cores 101, arranged in an amorphous $SiO_2$ matrix 103, wherein the $ZrO_2$ crystals are surrounded by a rim 102 comprising an IGF that comprises at least one hardness-enhancing additive. Such a material may be prepared in a method comprising steps 11-14.

Densification is a process of reducing the porosity in a material, i.e. making it denser. The sintering process controls the densification. Densification of a material usually occurs at high temperatures, for example 1100-1550° C., or 1150-1200° C.

In one embodiment of the third aspect, there is a dental restorative material comprising a densified material. The densified material is shaped into the shape of a human tooth and used as a dental restorative material. Such dental restorative material comprises a glass ceramic material according to the invention, comprising an amorphous $SiO_2$ matrix 103, $ZrO_2$ crystals in the form of cores 101 and a rim 102 comprising an IGF that comprises at least one hardness-enhancing additive. The $ZrO_2$ crystals in the cores 101 are at least partly surrounded by the rim 102.

All variants and examples of the third aspect can be combined with the first and second aspect unless expressly stated otherwise.

EXAMPLES

Three different sets of glass ceramic materials were prepared, one comprising yttrium as hardness-enhancing additive and one comprising aluminium as hardness-enhancing additive and one with no additive. All materials were prepared using the method comprising steps 11-14 illustrated in FIG. 3. All formed materials were evaluated in terms of mechanical and optical properties.

A fourth set of material were prepared comprising a mixture of hardness-enhancing additive. The fourth set were evaluated in terms of mechanical properties.

Example 1: $Y_2O_3$—$ZrO_2$—$SiO_2$ Material

Synthesis: Four different $Y_2O_3$—$ZrO_2$—$SiO_2$ samples (named Y-1 to Y-4) were fabricated by a sol-gel method wherein tetraethyl orthosilicate (TEOS) (Sigma-Aldrich, St Louis, MO, USA) and zirconium n-propoxide $Zr(OPr)_4$ (70 wt % in 1-propanol from Sigma-Aldrich) were used as the starting alkoxide precursors materials for $SiO_2$ and $ZrO_2$, respectively. HCl was added as a catalyst. $YCl_3$ powder was added into the mixed sol before final hydrolysis and polymerization. $YCl_3$ dissolved in the sol, did not show significant effect on the hydrolysis and polymerization processes of the mixed sol. The obtained sol-gel powder was calcined at 600° C. for 1 h in a muffle furnace to remove organics from precursors. Disc samples were obtained by hot pressing (Y1) or SPS (Y2-Y4), with a holding temperature of 1280° C., a holding time of 1 h, and an applied pressure of 36 MPa. The samples had the following compositions, in molar % and in weight %:

| Sample name | Compositions in molar % | | | Compositions in weight % | | |
|---|---|---|---|---|---|---|
| | $SiO_2$ | $ZrO_2$ | $Y_2O_3$ | $SiO_2$ | $ZrO_2$ | $Y_2O_3$ |
| Y-1 | 34 | 63 | 1.5 | 50.4 | 45.5 | 4.1 |
| Y-2 | 41.1 | 56.4 | 2.5 | 56.1 | 37.6 | 6.3 |

-continued

| | Compositions in molar % | | | Compositions in weight % | | |
|---|---|---|---|---|---|---|
| Sample name | $SiO_2$ | $ZrO_2$ | $Y_2Q_3$ | $SiO_2$ | $ZrO_2$ | $Y_2O_3$ |
| Y-3 | 30.8 | 66.7 | 2.5 | 45.3 | 47.9 | 6.8 |
| Y-4 | 20.5 | 77 | 2.5 | 32.7 | 60.0 | 7.3 |

The contents in molar % of the precursor materials were:

| Sample name | $SiO_2$ | $ZrO_2$ | $Y^{3+}$ |
|---|---|---|---|
| Y-1 | 34 | 63 | 3 |
| Y-2 | 40 | 55 | 5 |
| Y-3 | 30 | 65 | 5 |
| Y-4 | 20 | 75 | 5 |

Sample Y-1 was analyzed in terms of phase analysis and microstructure. Samples Y-2, Y-3 and Y-4 were analyzed in therms of mechanical properties.

Material characterization: The phase analysis was performed by X-ray diffraction (XRD) on a D8 Advanced diffractometer (Bruker Corporation, Billerica, MA). The data were acquired with Ni-filtered Cu $K_\alpha$ radiation (40 kV, 40 mA) in the 2θ interval between 20 and 80°, with a scan step of 5 s/step and a size of 0.0102°. The quantitative phase composition analysis was obtained from Rietveld refinement using Profex software. For transmission electron microscopy (TEM) analysis, an electron transparent lamella of the Y-1 and Y-3 samples was prepared with a dual beam focused ion beam-scanning electron microscope (FIB-SEM, FEI Strata DB325) and attached to Cu lift-out grid. The analysis was carried out on a probe corrected FEI Titan Themis equipped with the SuperX system for energy dispersive X-ray spectroscopy (EDS). The EDS elemental maps were acquired and quantified with the Esprit software developed by Bruker.

The mechanical properties of the samples were evaluated in terms of Young's modulus, nanohardness, microhardness and fracture toughness. The Young's modulus and hardness measurements were carried out on a nanoindentation tester (Ultra nanoindenter, CSM instruments) with a load of 8000 μN at a speed of 8000 μN/min. 10 indentations with proper distance from each other were performed for each sample. Young's modulus was calculated according to Oliver-Pharr method (equation 1):

$$E = \frac{1-\gamma^2}{(2\beta - S_U)\sqrt{A/\pi - (1-\gamma_i^2)/E_i}} \quad (1)$$

where γ is the Poisson ratio, β is the Oliver-Parr constant, $S_u$ is the slope at start of the unloading curve, A is indenter area function, $\gamma_i$ and $E_i$ are Poisson's ratio and Young's modulus of indenter material, respectively.

A microhardness tester (Buehler Micromet 2104, Lake Bluff, IL, USA) was used to measure the Vickers hardness on the micro scale with an indentation load of 19.6 N. 10 indentations were preformed on each sample. The length of crack and indentation diagonal were measured using the equipped software on the instrument. The fracture toughness was calculated by the Palmquvist method.

Figure 4:
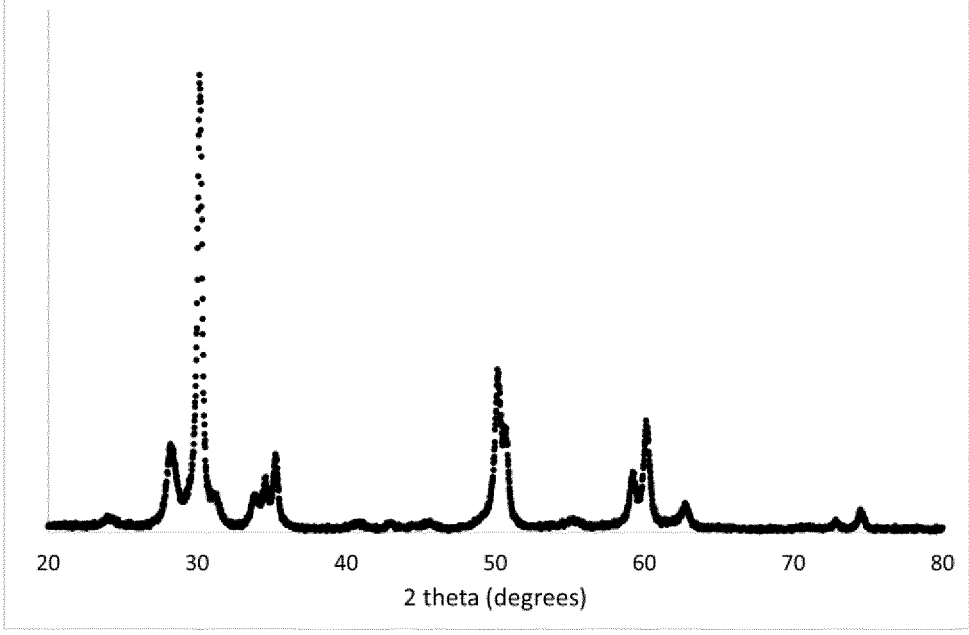
FIG. 4 is a graph showing an XRD pattern of one embodiment of the invention.

Results: XRD pattern, FIG. 4, for the Y-1 sample shows that the Y-3 sample was mainly composed of t-$ZrO_2$, while small diffraction peaks belonging to m-$ZrO_2$ phase were also found (at 27.8° and 31.1°), indicating that a certain amount of t-$ZrO_2$ transformed to m-$ZrO_2$ during the sintering process. $SiO_2$ was X-ray amorphous since no obvious peaks belonging to crystalline forms were found in the XRD patterns. Quantification results by Rietveld refinement demonstrated that the Y-1 sample contained 90.6 wt % t-$ZrO_2$ and 9.4 wt % m-$ZrO_2$.

The microstructure of the Y-1 sample was characterized by scanning transmission electron microscopy (STEM) technique. STEM-bright field (BF) images (FIG. 5a) show an overview of the microstructure. The parts with darker contrast are $ZrO_2$ crystals, while the 'background' with brighter contrast corresponded to the amorphous $SiO_2$ matrix. Thus, the basic structural characteristic of the Y-1 sample is $ZrO_2$ crystals embedded in an amorphous $SiO_2$ matrix. The majority of the $ZrO_2$ crystals had an ellipsoidal morphology, i.e. shape, and their sizes generally ranged from 40 nm to 60 nm in diameter. In FIG. 5b, particles with bright contrast are $ZrO_2$ crystals, since in the STEM-high angle annular dark field (HAADF) imaging mode the contrast is proportional to the atomic number (Z), and heavier atoms appear brighter. Most of the $ZrO_2$ crystals, were connected with their adjacent crystals by grain boundary in at least one direction. The crystals and matrix were confirmed as $ZrO_2$ and $SiO_2$, respectively, by STEM-EDS maps (not shown). Oxygen elements was nearly homogenously distributed in both $ZrO_2$ crystals and $SiO_2$ matrix, with slightly concentrated distribution in $ZrO_2$ crystals. Y element distributed both around and within the $ZrO_2$ crystals. Slightly more intense Y signals were detected at the $ZrO_2$/$SiO_2$ interfaces and at the grain boundaries between $ZrO_2$ crystals, indicating that there was concentrated Y distribution at those two regions. No obvious Y signal were detected in the $SiO_2$ matrix.

The elemental distribution of the grain boundary appearance with a layer of intergranular phase was examined with STEM-EDS line scanning and the results are shown in FIGS. 6a, b and c. It can be observed that Y segregated in the intergranular phase (IGF, marked I in FIGS. 6b and c), i.e. in the area in between the adjacent $ZrO_2$ crystals. In FIG. 6b the different elements have different marks: ■ is for O, ☆ is for Si, ◆ is for Zr, and ▼ is for Y. In FIG. 6c ■ is for Si and ● is for Y. FIG. 6a is a STEM-HAADF image showing connected $ZrO_2$ crystals and a thin layer of IGF between the $ZrO_2$ crystals. A STEM-EDS line scan was carried out along the white arrow line and the distribution of O, Si, Y, and Zr elements along the white arrow line is shown in FIG. 6b, from which it can be observed that Y and Si elements showed higher atomic ratio between point 30 and point 40, indicating that this region was rich in Y and Si. Meanwhile, the atomic ratio of Zr in this region was lower than in other regions. O elements showed homogenous distribution along the scan line, without obvious rich or deficient regions. To further analyze the distribution of Y and Si along the scan line, the data of these two elements were plotted separately as displaced in FIG. 6c. FIG. 6c shows that the IGF was rich in Y (marked I in FIG. 6c).

Samples Y-2, Y-3 and Y-4 were evaluated in terms of mechanical properties. The results are summarized in Table 1, together with the wt % for the compositions.

TABLE 1

Y$_2$O$_3$-ZrO$_2$-SiO$_2$ compositions (in wt % and molar %) and corresponding mechanical properties. The table shows the numbers ± standard deviation (STD).

| Composition (molar %) | | | Composition (wt %) | | | Mechanical properties | | | |
|---|---|---|---|---|---|---|---|---|---|
| | | | | | | Youngs modulus | Nano-hardness | Micro-hardness | Fracture toughness |
| SiO$_2$ | ZrO$_2$[1] | Y$_2$O$_3$ | SiO$_2$ | ZrO$_2$[1] | Y$_2$O$_3$ | (GPa) | (GPa) | (GPa) | (MPa · m$^{1/2}$) |
| 41.1 | 56.4 | 2.5 | 24.7 | 69.6 | 5.7 | 140.55 ±4.25 | 10.75 ±0.33 | 9.96 ±0.19 | 5.71 ± 0.19 |
| 30.8 | 66.7 | 2.5 | 17.4 | 77.3 | 5.3 | 168.45 ±4.49 | 11.61 ±0.22 | 10.57 ±0.15 | 6.36 ± 0.13 |
| 20.5 | 77 | 2.5 | 10.9 | 84.1 | 5.0 | 181.28 ±7.03 | 12.72 ±0.36 | 10.88 ±0.56 | 5.47 ± 0.23 |

[1]All ZrO$_2$ was in the form of t-ZrO$_2$, as determined by PXRD

Example 2: Al$_2$O$_3$—ZrO$_2$—SiO$_2$ Material

Synthesis: Three different Al$_2$O$_3$—ZrO$_2$—SiO$_2$ samples were prepared using a sol-gel method wherein tetraethyl orthosilicate (TEOS) (Sigma-Aldrich, St Louis, MO, USA) and zirconium n-propoxide Zr(OPr)$_4$ (70 wt % in 1-propanol from Sigma-Aldrich) were used as the starting alkoxide precursor materials for SiO$_2$ and ZrO$_2$, respectively. HCl was added as a catalyst. Al(O-i-Pr)$_3$ powder was added into the mixed sol before final hydrolysis and polymerization. Al(O-i-Pr)$_3$ dissolved in the sol, and did not show significant effect on the hydrolysis and polymerization processes of the mixed sol. The obtained sol-gel powder was calcined at 600° C. for 1 h in a muffle furnace to remove organics from precursors. Disc samples were obtained by SPS, with a holding temperature of 1150° C., a holding time of 5 min, and an applied pressure of 60 MPa. The samples had the following compositions, in molar % and in wt %:

| Sample name | Composition in molar % | | | Composition in wt % | | |
|---|---|---|---|---|---|---|
| | SiO$_2$ | ZrO$_2$ | Al$_2$O$_3$ | SiO$_2$ | ZrO$_2$ | Al$_2$O$_3$ |
| Al-1 | 30.8 | 66.7 | 2.5 | 17.9 | 79.6 | 2.5 |
| Al-2 | 36.0 | 61.5 | 2.5 | 21.7 | 75.8 | 2.5 |
| Al-3 | 32 | 63 | 5 | 18.9 | 76.1 | 5.0 |

The contents in molar % of the precursor materials were:

| Sample name | SiO$_2$ | ZrO$_2$ | Al$^{3+}$ |
|---|---|---|---|
| Al-1 | 30 | 65 | 5 |
| Al-2 | 35 | 60 | 5 |
| Al-3 | 30 | 60 | 10 |

Material characterization: The phase analysis of the samples was performed by X-ray diffraction (XRD) on a D8 Advanced diffractometer (Bruker Corporation, Billerica, MA). The data were acquired with Ni-filtered Cu K$_\alpha$ radiation (40 kV, 40 mA) in the 2θ interval between 20 and 80°, with a scan step of 5 s/step and a size of 0.0102°. For transmission electron microscopy (TEM) analysis, an electron transparent lamella of the Al-3 sample was prepared with a dual beam focused ion beam-scanning electron microscope (FIB-SEM, FEI Strata DB325) and attached to Cu lift out grid. The analysis was carried out on a probe corrected FEI Titan Themis equipped with the SuperX system for energy dispersive X-ray spectroscopy (EDS). The EDS elemental maps were acquired and quantified with the Esprit software developed by Bruker.

The mechanical properties of the samples were evaluated in terms of Young's modulus, nanohardness, microhardness and fracture toughness. The Young's modulus and hardness measurements were carried out on a nanoindentation tester (Ultra nanoindenter, CSM instruments) with a load of 8000 μN at a speed of 8000 μN/min. 10 indentations with proper distance from each other were performed for each sample. Young's modulus was calculated according to Oliver-Pharr method (equation 1):

$$E = \frac{1 - \gamma^2}{(2\beta - S_U)\sqrt{A/\pi - (1 - \gamma_i^2)/E_i}} \tag{1}$$

where γ is the Poisson ratio, β is the Oliver-Parr constant, S$_u$ is the slope at start of the unloading curve, A is indenter area function, γ$_i$ and E$_i$ are Poisson's ratio and Young's modulus of indenter material, respectively.

A microhardness tester (Buehler Micromet 2104, Lake Bluff, IL, USA) was used to measure the Vickers hardness on the micro scale with an indentation load of 19.6N. 10 indentations were preformed on each sample. The length of crack and indentation diagonal were measured using the equipped software on the instrument. The fracture toughness was calculated by the Palmquvist method.

Figure 7:
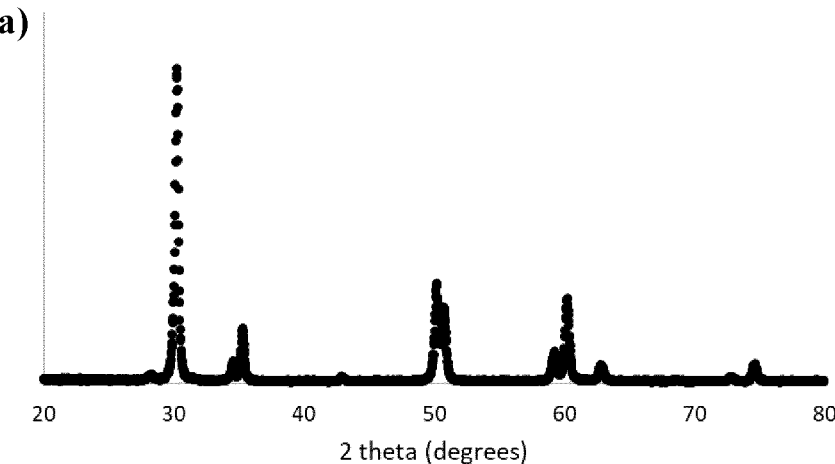
FIGS. 7 *a-c* are XRD patterns of embodiments of the invention.
Figure 7:
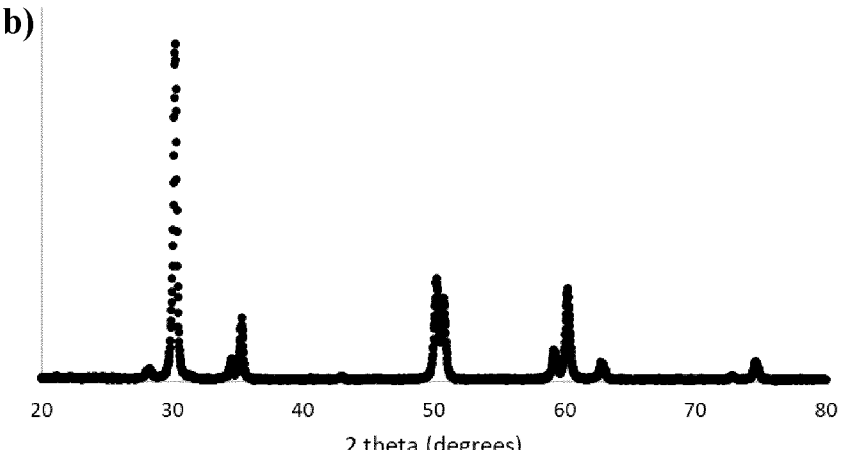
Figure 7:
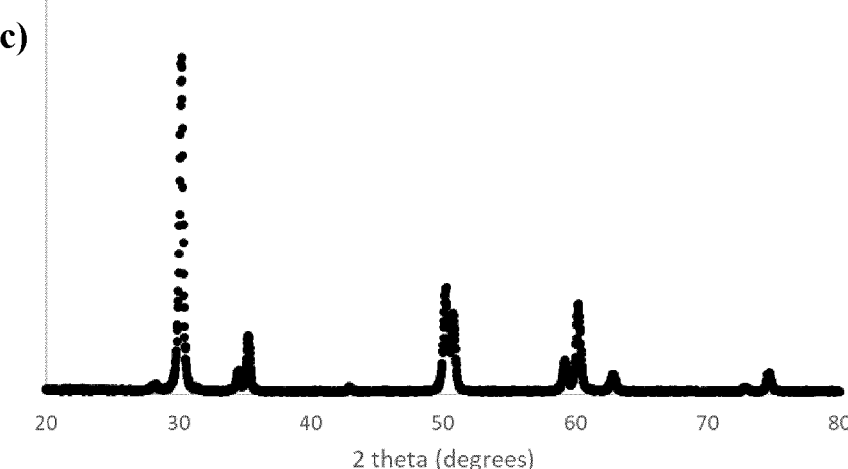

Results: XRD patterns, FIGS. 7 a-c, for the bulk samples after hot pressing show that all samples were mainly composed of t-ZrO$_2$, FIG. 7a shows sample Al-1, FIG. 7b shows sample Al-2, and FIG. 7c show sample Al-3, while small diffraction peaks belonging to m-ZrO$_2$ phase were also found (at 27.8° and 31.1°) in samples Al-1, see FIGS. 7a, and Al-2, see FIG. 7b, indicating that a certain amount of t-ZrO$_2$ transformed to m-ZrO$_2$ during the sintering process. In all three samples, SiO$_2$ was X-ray amorphous since no obvious peaks belonging to crystalline forms were found in the XRD patterns.

Figure 8:
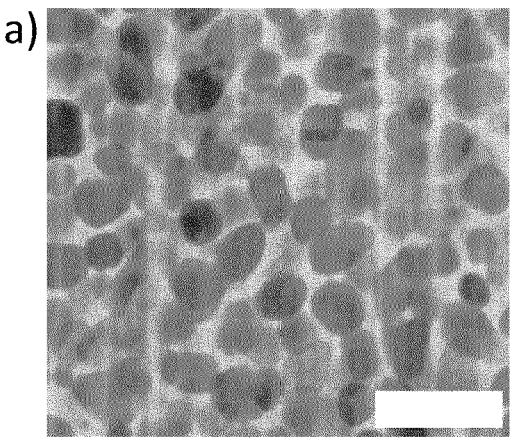
FIGS. 8 *a-e* are STEM images of one embodiment of the invention a) with a 100 nm scale bar, b) with a 10 nm scale bar, c) with a 2 nm scale bar, d) with a 2 nm scale bar and e) with a 2 nm scale bar.
Figure 8:
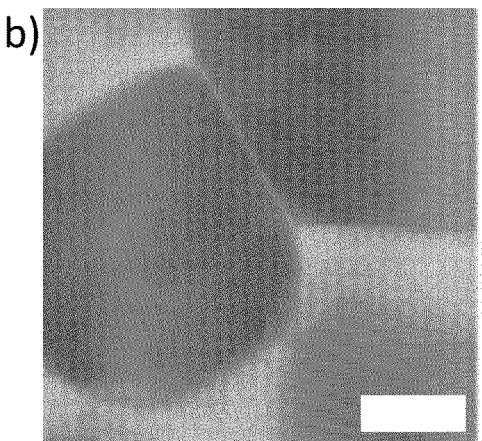
Figure 8:
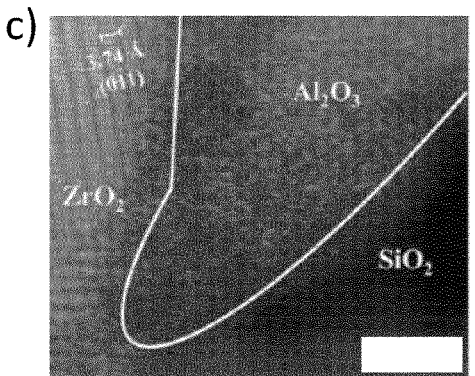
Figure 8:
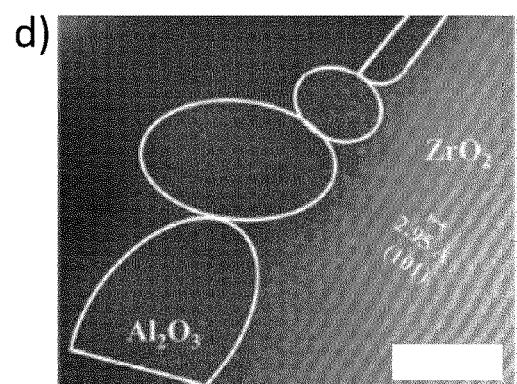
Figure 8:
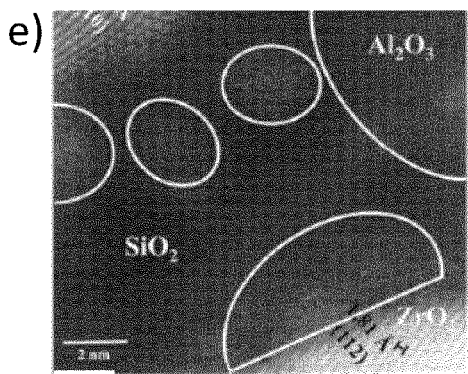

The microstructure of the Al-3 sample was characterized by scanning transmission electron microscopy (STEM) technique, FIGS. 8 a-e. STEM-bright field (BF) image (FIG. 8a) demonstrated an overview of the microstructure. The parts with darker contrast were ZrO$_2$ crystals, while the 'background' with brighter contrast corresponded to amorphous SiO$_2$ matrix, see FIG. 8a. Thus, the basic structural characteristic of the Al-3 sample was ZrO$_2$ crystals embedded in an amorphous SiO$_2$ matrix. The majority of ZrO$_2$ crystals had an ellipsoidal morphology and their diameters generally ranged from 40 nm to 60 nm. In FIG. 8*b*, particles with bright contrast were $ZrO_2$ crystals, since in the STEM-high angle annular dark field (HAADF) imaging mode, the contrast is proportional to the atomic number (Z), and heavier atoms appear brighter. Most of the $ZrO_2$ crystals were connected with their adjacent particles by grain boundary in at least one direction. The crystals and matrix were confirmed as $ZrO_2$ and $SiO_2$, respectively, by STEM-EDS maps (not shown). Oxygen elements was nearly homogenously distributed in both the $ZrO_2$ crystals and the $SiO_2$ matrix, with slightly concentrated distribution in the $ZrO_2$ crystals. The Al element was distributed around the $ZrO_2$ crystals. More intense Al signals were detected at the $ZrO_2/SiO_2$ interfaces and at the grain boundaries between adjacent $ZrO_2$ crystals, indicating that there was concentrated Al distribution at those two regions. No obvious Al signal was detected in the $SiO_2$ matrix or in the $ZrO_2$ crystals.

Figure 9:
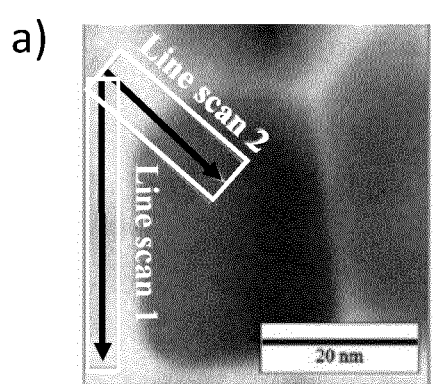
FIGS. 9 *a-e* are graphs showing show line scans of one embodiment of the invention, a) is a STEM image with 20 nm scale bar, b) is a STEM image with a 10 nm scale bar, c) is a graph showing the concentration in at %, d) is a graph showing the concentration in at % and e) is a graph showing the concentration in at %.
Figure 9:
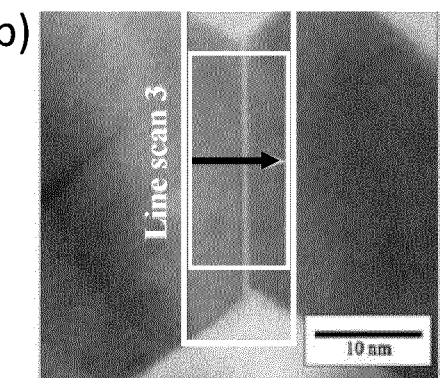
Figure 9:
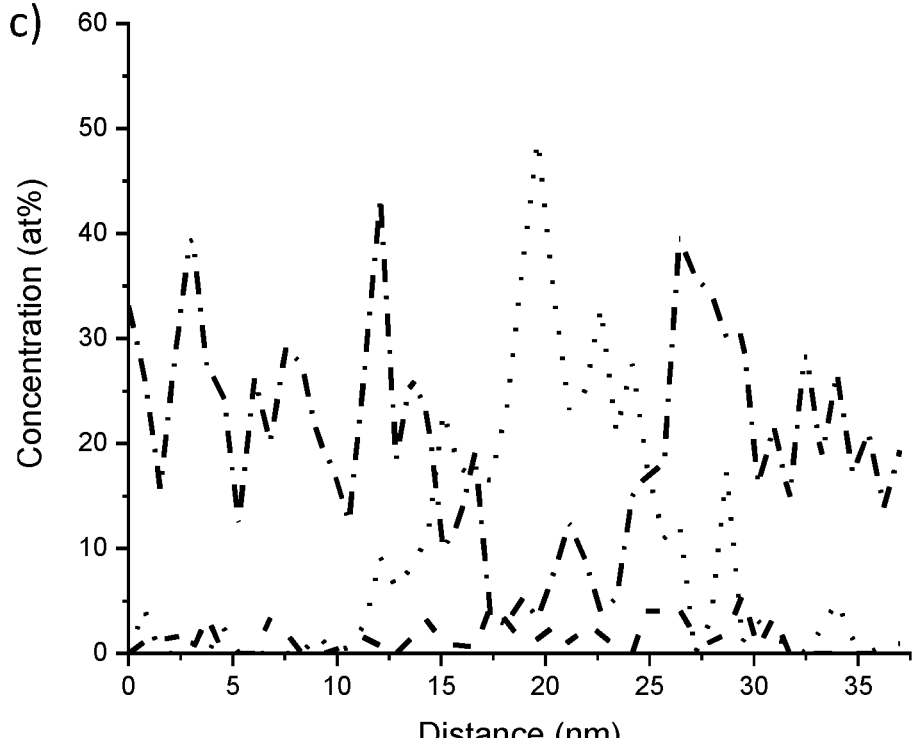
Figure 9:
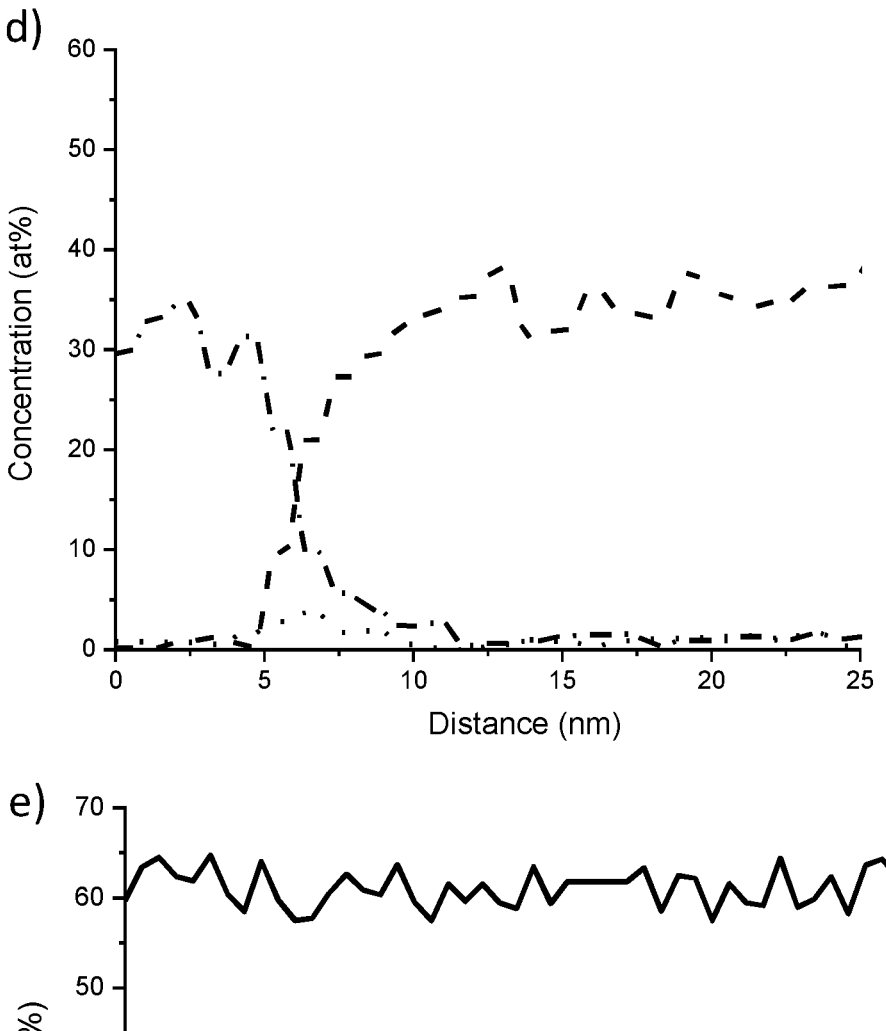

The elemental distribution of the grain boundary with a layer of intergranular phase was examined with STEM-EDS line scanning and the results are shown in FIGS. 9*a-e*. It can be observed in FIGS. 9*a* and *b* that Al segregated in the intergranular phase (IGF). FIG. 9*a* is a STEM-HAADF image showing connected $ZrO_2$ crystals and a thin layer of IGF between the $ZrO_2$ crystals. STEM-EDS line scans were carried out along the black line arrows marked "Line scan 1", "Line scan 2" and "Line scan 3". FIG. 9*c* shows the results from Line scan 1 showing that region between approximately 15 and 25 nm in distance had a high concentration of Al (line • •, i.e. dotted) and low concentration of Si (line - • -, i.e. dashed/dotted) and Zr (line - - -, i.e. dashed). FIG. 9*d* shows the results from Line scan 2 showing that region between 5 and 10 nm in distance had a high concentration of Al than the region below 5 nm and high 10 nm, the lines in FIG. 9*d* has the same marks as in FIG. 9*c*. FIG. 9*e* shows the results from Line scan 3, i.e. the IGF region, showing that the region between 4 and 6 nm in distance had a high concentration of Al. The lines in FIG. 9*e* has the same marks as the lines in FIGS. 9 *c* and *d* with the addition that the solid line represent 0.

All three samples were evaluated in terms of mechanical properties, the results are summarized in Table 2, together with the wt % of the compositions.

TABLE 2

Al2O3-ZrO2-SiO2 compositions (in wt % and mol %) and corresponding mechanical properties. The table shows the numbers ± standard deviation (STD).

| Composition (mol %) | | | Compositions (wt %) | | | Mechanical properties | | | |
|---|---|---|---|---|---|---|---|---|---|
| | | | | | | Youngs modulus | Nano-hardness | Micro-hardness | Fracture toughness |
| $SiO_2$ | $ZrO_2$[1] | $Al_2O_3$ | $SiO_2$ | $ZrO_2$[1] | $Al_2O_3$ | (GPa) | (GPa) | (GPa) | (MPa · m$^{1/2}$) |
| 30.8 | 66.7 | 2.5 | 17.4 | 79.6 | 2.5 | 146.1 ±4.0 | 11.61 ±0.49 | 8.66 ±0.17 | 5.70 ± 0.26 |
| 36.0 | 61.5 | 2.5 | 21.7 | 75.8 | 2.5 | 135.1 ±2.5 | 10.82 ±0.15 | 8.54 ±0.15 | 5.34 ± 0.08 |
| 32.0 | 63 | 5 | 18.9 | 76.1 | 5.0 | 164.1 ±2.9 | 12.87 ±0.44 | 9.10 ±0.31 | 8.82 ± 0.48 |

[1]At least more than 90 wt % of the $ZrO_2$ was in the form of t-$ZrO_2$, as determined by PXRD

Example 3 (Comparative Example): $ZrO_2$—$SiO_2$ Material

Synthesis: Three different $ZrO_2$—$SiO_2$ samples without hardness-enhancing additive were prepared for comparative testing. The samples were prepared using a sol-gel method wherein tetraethyl orthosilicate (TEOS) (Sigma-Aldrich, St Louis, MO, USA) and zirconium n-propoxide $Zr(OPr)_4$ (70 wt % in 1-propanol from Sigma-Aldrich) were used as the starting alkoxide precursor materials for $SiO_2$ and $ZrO_2$, respectively. The obtained sol-gel powder was calcined at 600° C. for 1 h in a muffle furnace to remove organics from precursors. Disc samples were obtained by SPS, with a holding temperature of 1150° C., a holding time of 5 min, and an applied pressure of 60 MPa. The samples had the following compositions, in molar %:

| Sample name | $SiO_2$ | $ZrO_2$ |
|---|---|---|
| SiZr-1 | 35 | 65 |
| SiZr-2 | 45 | 55 |
| SiZr-3 | 55 | 45 |

The three SiZr samples were analysed for phase composition and mechanical properties as describes in Examples 1 and 2. The phase analysis showed that the materials were mainly composed of t-$ZrO_2$. The mechanical properties are shown in Table 3 below together with the wt % of the compositions.

TABLE 3

ZrO$_2$-SiO$_2$ compositions (wt % and mol %) and corresponding mechanical properties. The table shows the numbers ± standard deviation (STD).

| | | | | Mechanical properties | | | |
|---|---|---|---|---|---|---|---|
| Composition (mol %) | | Composition (wt %) | | Youngs modulus | Nano-hardness | Micro-hardness | Fracture toughness |
| SiO$_2$ | ZrO$_2$[1] | SiO$_2$ | ZrO$_2$[1] | (GPa) | (GPa) | (GPa) | (MPa · m$^{1/2}$) |
| 35 | 65 | 20.8 | 79.2 | 152.5 ±8.8 | 10.55 ±0.52 | 7.21 ±0.10 | 6.55 ± 0.29 |
| 45 | 55 | 28.5 | 71.7 | 142.0 ±4.7 | 9.58 ±0.59 | 7.16 ±0.03 | 5.48 ± 0.23 |
| 55 | 45 | 37.4 | 62.6 | 117.0 ±4.4 | 9.02 ±0.73 | 7.57 ±0.11 | 4.15 ± 0.53 |

Example 4: MnO$_x$—Al$_2$O$_3$—ZrO$_2$—SiO$_2$ Material

A set of additional ZrO$_2$—SiO$_2$ samples were prepared comprising MnO$_x$ and Al$_2$O$_3$ as hardness-enhancing additive. Four samples were prepared with MnO$_x$ content ranging from 0 to 0.33 wt % (0 to 0.5 molar %). The samples were sinterted using pressure less with a holding temperature of 1170° C., a ramping rate of 3° C./min, and a holding time of 5-10 hours with 3 samples/group.

The biaxial strength of the samples were tested. The results can be seen in Table 4 below.

TABLE 4

ZrO$_2$-SiO$_2$ compositions (mol % and wt %) and corresponding mechanical properties. The table shows the numbers ± standard deviation (STD).

| Composition (mol %) | | | | Composition (wt %) | | | | SiO$_2$:ZrO$_2$: | Biaxial strength |
|---|---|---|---|---|---|---|---|---|---|
| SiO$_2$ | ZrO$_2$ | Al$_2$O$_3$ | MnO$_x$ | SiO$_2$ | ZrO$_2$ | Al$_2$O$_3$ | MnO$_x$ | Al$_2$O$_3$:MnO$_x$ | (MPa) |
| 50 | 45 | 5 | 0 | 33.17 | 61.20 | 3.32 | 0.00 | 1:0.9:0.1 | 300.1 ± 77.4 |
| 50 | 45 | 4.9 | 0.1 | 33.18 | 61.21 | 3.25 | 0.07 | 1:0.9:0.098:0.002 | 345.6 ± 66.8 |
| 50 | 45 | 4.75 | 0.25 | 33.19 | 61.22 | 3.15 | 0.17 | 1:0.9:0.095:0.005 | 534.3 ± 35.5 |
| 50 | 45 | 4.5 | 0.5 | 33.20 | 61.25 | 2.99 | 0.33 | 1:0.9:0.09:0.01 | 615 ± 84.7 |

The invention claimed is:

1. A glass ceramic material comprising zirconium dioxide crystals embedded in an amorphous silicon dioxide matrix and at least one hardness enhancing additive, wherein the zirconium dioxide crystals form cores and the cores are at least partly surrounded by rims, wherein the rims comprise an intergranular phase, and wherein the intergranular phase comprises at least silicon dioxide, zirconium dioxide and at least one hardness-enhancing additive, and wherein the concentration in weight percent of the hardness-enhancing additive is higher in the rims than in the amorphous silica matrix and in the cores.

2. The glass ceramic material according to claim 1, wherein at least a portion of the cores are connected with at least one adjacent other core forming a grain boundary between the cores, and wherein the concentration of hardness-enhancing additive is higher in the grain boundaries than in the parts of the rim in contact with the silicon dioxide matrix.

3. The glass ceramic material according to claim 1, wherein the material comprises 2-10 weight % of hardness-enhancing additive.

4. The glass ceramic material according to claim 1, wherein the intergranular phase is amorphous.

5. The glass ceramic material according to claim 1, wherein at least 90%, or at least 95% of the zirconium dioxide crystals have an average crystal size of 100 nm or less.

6. The glass ceramic material according to claim 1, wherein the zirconium dioxide crystals have an ellipsoidal shape.

7. The glass ceramic material according to claim 1, wherein the zirconium dioxide comprises either tetragonal zirconium dioxide or a mixture of tetragonal zirconium dioxide and monoclinic zirconium dioxide, wherein at least 80% of the zirconium dioxide crystals are tetragonal zirconium dioxide, as determined by Rietveld refinement.

8. The glass ceramic material according to claim 1, wherein the hardness-enhancing additive comprises at least one of aluminum oxide and yttrium oxide.

9. The glass ceramic material according to claim 8, wherein the material comprises 2-10 weight % hardness-enhancing additive in the form of at least one of yttrium oxide or aluminum oxide.

10. A method of forming a glass ceramic according to claim 1, wherein the method comprises the following steps:

(11): mixing of two sols, the first sol comprises a zirconium dioxide precursor material and the second sol comprises a silicon dioxide precursor material, adding a catalyst to the mixture of two sols, and wherein said step comprises adding a precursor material for a hardness-enhancing additive;

(12): drying and forming of a xerogel;

(13): calcination of the formed xerogel; and (14): sintering of the calcined xerogel, wherein the method comprises a fractionation step reducing the particle size of a material obtained in step 11.

11. The method according to claim 10, wherein, in step 11, the first or the second sol comprises the precursor material for the hardness-enhancing additive.

12. The method according to claim 11, wherein the precursor material for the hardness-enhancing additive is added to the two sols after they are mixed in step 11.

13. The method according to claim 10, wherein 3-20 molar %, based on the total molar amount of the material, of the precursor material for the hardness-enhancing additive, calculated as the content of at least one of $Y^{3+}$ or $Al^{3+}$ is added.

14. The method according to claim 10, wherein the sintering in step (14) of the method is performed using hot pressing (HP), hot isostatic pressure (HIP) or spark plasma sintering (SPS).

15. A densified material comprising the glass ceramic according to claim 1.

16. A dental restorative material comprising the densified material according to claim 15.

\*   \*   \*   \*   \*